United States Patent
van der Klugt et al.

(10) Patent No.: US 11,096,834 B2
(45) Date of Patent: Aug. 24, 2021

(54) PROCESS FOR MAKING FIBROUS LAYERS HAVING CHANNELS FOR ABSORBENT ARTICLES

(71) Applicant: The Procter & Gamble Company, Cincinnati, OH (US)

(72) Inventors: Walter Pieter Hendrik Laurentius van der Klugt, Mechernich (DE); Ute Fröhlich, Frankfurt (DE); Ernesto Gabriel Bianchi, Oberursel (DE)

(73) Assignee: The Procter & Gamble Company, Cincinnati, OH (US)

( * ) Notice: Subject to any disclaimer, the term of this patent is extended or adjusted under 35 U.S.C. 154(b) by 84 days.

(21) Appl. No.: 16/541,332

(22) Filed: Aug. 15, 2019

(65) Prior Publication Data
US 2020/0060881 A1 Feb. 27, 2020

(30) Foreign Application Priority Data
Aug. 21, 2018 (EP) .................................... 18189974

(51) Int. Cl.
| | |
|---|---|
| *A61F 13/15* | (2006.01) |
| *B29C 70/50* | (2006.01) |
| *B29C 65/00* | (2006.01) |
| *B29C 70/54* | (2006.01) |
| *B29L 31/48* | (2006.01) |

(52) U.S. Cl.
CPC .. *A61F 13/15658* (2013.01); *A61F 13/15723* (2013.01); *A61F 13/15739* (2013.01); *B29C 66/729* (2013.01); *B29C 70/504* (2013.01); *B29C 70/545* (2013.01); *A61F 2013/15715* (2013.01); *B29K 2995/0068* (2013.01); *B29L 2031/4878* (2013.01)

(58) Field of Classification Search
CPC ......... Y10T 156/1057; A61F 13/15658; A61F 13/15626; A61F 2013/15715; B29C 70/545
See application file for complete search history.

(56) References Cited

U.S. PATENT DOCUMENTS

| | | |
|---|---|---|
| 4,515,595 A | 5/1985 | Kievit |
| 4,710,189 A | 12/1987 | Lash |
| 5,221,274 A | 6/1993 | Buell |
| (Continued) | | |

FOREIGN PATENT DOCUMENTS

| | | |
|---|---|---|
| EP | 2886093 A1 | 6/2015 |
| WO | WO2004011723 A3 | 4/2004 |
| (Continued) | | |

OTHER PUBLICATIONS

EP International Search Report, dated Feb. 13, 2019, 9 pages.

*Primary Examiner* — Mark A Osele
*Assistant Examiner* — Christopher C Caillouet
(74) *Attorney, Agent, or Firm* — Jay A. Krebs

(57) ABSTRACT

Process for making discrete fibrous layers, comprising the steps of continuously depositing fibers in an endless series of molds, with two neighboring molds connected by a connecting section, transferring the resulting continuous fibrous layer to another endless moving surface and cutting the continuous fibrous layer at the connecting sections to form discrete fibrous layers. The molds comprise at least one raised element that prevents fiber deposition in the raised element area.

16 Claims, 7 Drawing Sheets

(56) References Cited

U.S. PATENT DOCUMENTS

| | | | |
|---|---|---|---|
| 5,466,409 A | 11/1995 | Partridge | |
| 6,336,922 B1 | 1/2002 | Vangompel | |
| 6,802,834 B2 * | 10/2004 | Melius | A61F 13/15626 |
| | | | 604/378 |
| 2004/0098838 A1 | 5/2004 | Venturino | |
| 2010/0198179 A1 * | 8/2010 | Noda | A61F 13/536 |
| | | | 604/365 |
| 2014/0305570 A1 * | 10/2014 | Matsunaga | A61F 13/15658 |
| | | | 156/62.2 |
| 2016/0074248 A1 * | 3/2016 | Rosati | A61F 13/55145 |
| | | | 604/378 |
| 2017/0312149 A1 * | 11/2017 | Bianchi | A61F 13/53747 |
| 2019/0000688 A1 * | 1/2019 | Bianchi | A61F 13/551 |

FOREIGN PATENT DOCUMENTS

| | | |
|---|---|---|
| WO | WO2012006300 A1 | 1/2012 |
| WO | WO2012170778 | 12/2012 |
| WO | WO2012177400 | 12/2012 |
| WO | WO2012177401 A1 | 12/2012 |
| WO | WO2014093310 A1 | 6/2014 |
| WO | WO2014093323 A1 | 6/2014 |
| WO | WO2014168810 A1 | 10/2014 |
| WO | WO2014200794 | 12/2014 |
| WO | WO2015031225 A1 | 3/2015 |
| WO | WO2015031229 A1 | 3/2015 |
| WO | WO2015031243 A1 | 3/2015 |
| WO | WO2017189188 A1 | 11/2017 |

\* cited by examiner

PROCESS FOR MAKING FIBROUS LAYERS HAVING CHANNELS FOR ABSORBENT ARTICLES

CROSS REFERENCE TO RELATED APPLICATION

This application claims priority under 35 U.S.C. § 119 to European Patent Application Serial No. 18189974.1, filed on Aug. 21, 2018, the entire disclosure of which is hereby incorporated by reference.

FIELD OF THE INVENTION

The invention relates to a process for making individual fibrous layers that can be used as component of absorbent articles such as diapers (including taped diapers and pant diapers). The process uses molds which are connected to each other by connecting sections. The molds also comprise one or more raised elements inside. The raised elements hinder the fibers from being substantially deposited, so that fiber free-channels corresponding to the raised elements are formed in the fibrous layer. The fibrous layers may be in particular used as distribution layers in an absorbent article such as a diaper.

BACKGROUND OF THE INVENTION

Absorbent articles for personal hygiene are designed to absorb and contain body exudates, in particular large quantity of urine. These absorbent articles comprise a fluid-permeable topsheet on the wearer-facing side, a fluid-impermeable backsheet on the garment-facing side and in-between an absorbent core comprising superabsorbent polymers.

Absorbent articles may also comprise one or more layers between the topsheet and the absorbent core whose function is to quickly acquire the fluid away from the surface of the article and distribute it to the underlying absorbent core. These layers are sometimes designated as acquisition layer, distribution layer or acquisition-distribution system when two layers are combined. A simple acquisition layer construction consists of a discrete layer of a nonwoven material disposed directly under the topsheet and comprising synthetic fibers, for example a thermobonded, latex bonded or through air bonded nonwoven. Acquisition layers are used in some products in combination with a distribution layer comprising cross-linked cellulose. Unlike absorbent cores, acquisition and distribution layers are free of superabsorbent polymers.

WO2014/093323A1 (Bianchi et al.) discloses a profiled distribution layer comprising cross-linked cellulose fibers supported on an acquisition layer. The distribution layer is rounded on one side and is shorter than the acquisition layer. The distribution layer may comprise channels which is discrete areas within the distribution layer that comprise no or substantially less fibers than the rest of the distribution layer. Distribution layers comprising channels are also disclosed for example in WO2015/031225A1, WO2015/031229A1 or WO2015/031243A1 (Roe et al.).

An apparatus and form for making an air formed fibrous web comprising channels is disclosed in WO2004/011723 (Venturino et al). The formed fibrous web is used to make an absorbent core. The channels described in this document do not extend through the whole thickness of the fibrous web. WO2017/189188 (Bianchi et al.) discloses a fibrous distribution layer comprising channels and zones having different basis weight. The forming molds for making the distribution layers do not have connecting sections in this document.

It would be desirable to improve in a cost efficient and simple way the process for making fibrous layer comprising channels. The fibrous layers may then be directly used as a distribution layer in an absorbent article such as a diaper.

SUMMARY OF THE INVENTION

The present invention relates to a process for making individual fibrous layers. The process comprises the steps of continuously depositing fibers in a plurality of molds disposed on an endless moving surface such as a drum, with two neighboring molds connected by a connecting section, continuously transferring the resulting continuous fibrous layer on another moving surface, and cutting the continuous fibrous layer through the area corresponding to the connecting sections to form individual fibrous layers. The molds comprise at least one raised element that hinders fibers deposition in this area so that at least one channel substantially free of fibers corresponding to the raised element is formed in the discrete fibrous layers (optionally after a scarfing step to remove excess fibers on the top of the raised element).

The inventors have found that laying the fibrous material as a continuous layer enables a better release from the moving endless surface (typically a drum) compared to making individual fibrous layers directly in discrete unconnected molds. The fibrous layers further comprise channels that need to be placed at a desired position relative to the other components in a finished article, especially since it may be desired to attach one overlaying layer such as a topsheet or an acquisition layer through the channels to an underlying layer such as the absorbent core. This means that the continuous layer of fibrous material must be cut into individual fibrous layers at a precise position to ensure registration and proper assembling of the different components of the article. The connecting sections can be used in the present invention also serve as cutting guides for the operator to register the cutting apparatus, which is especially important at the high production speed of a modern converting line. The connecting sections may in particular define a neck between two molds, resulting in individual fibrous layers having a narrower width at their front and back edges.

Other advantageous optional features of the present invention are addressed in the following description and Figures; however these are not intended to limit the scope of the claims unless specifically indicated. For example, the continuous fibrous layer may be unmolded on a support layer, such as a nonwoven, which may be cut at the same time as the fibrous layer to make individual laminate structures. The support layer may be for example a nonwoven that can be used as an acquisition layer and the fibrous layer as a distribution layer. The fibrous layer, with or without the support layer, may be combined in a further step with an absorbent core material and/or a topsheet material.

For ease of discussion, the examples of the invention are discussed below with reference to these Figures and the numerals referred therein, however these are not intended to limit the scope of the claims unless specifically indicated.

DETAILED DESCRIPTION OF THE INVENTION

Figure 1:
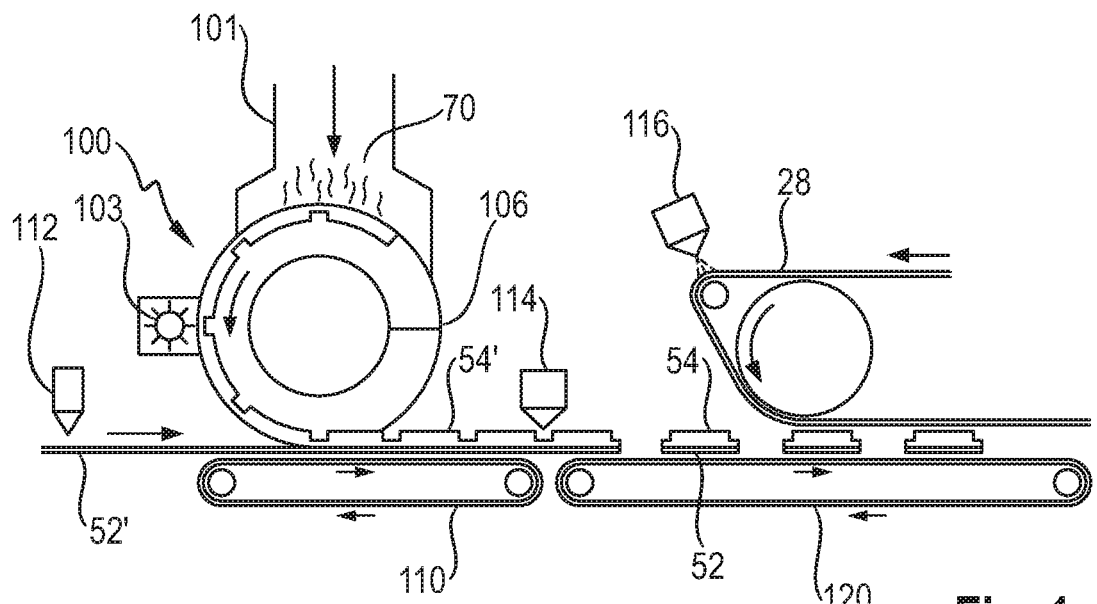
FIG. 1 shows a schematic sketch of a process according to the invention for making individual fibrous layers, with a further optional step of combining them with a stream of absorbent cores.

General Description of the Process with Reference to FIG. 1

FIG. 1 illustrates schematically the process of the invention. The left side of the Figure illustrates an airlaying apparatus comprising a first endless moving surface 100 in the form of a rotating drum. The drum comprises on its periphery a plurality of molds 102 for receiving and forming fibers 70. The drum 100 and some of its components are shown in a more detailed view in FIGS. 2-3. Other ancillary equipments for the airlaying apparatus that are schematically represented include a forming chamber 101 for concentrating and directing the fibers 70 into the molds 102 of the drum and a scarfing unit 103 for removing excess fibers at the surface of the molds after these have left the forming chambers. This type of airlaying apparatus is in itself standard in the industry and is not discussed herein in details, reference being made for example to prior art reference WO2004/011723, Venturino et al, which explains in details the functioning of such apparatus, including how the fibers may be individualized using a fiberizer (not shown), how a negative pressure (vacuum) is used to direct the fibers onto the deposition molds while in the forming chambers, and how the scarfing unit 103 removes and recycles excess fibers deposited in the molds 102.

The fibers 70 which are deposited may be mixed with superabsorbent particles ("SAP") to make conventional airfelt cores comprising a mix of SAP and cellulose fibers, as is known in the art. While the process described herein may thus be used to make absorbent cores, the invention will be further illustrated for making distribution layers 54 free of SAP, that can be combined with an absorbent core 28. The right side of the FIG. 1 illustrates for example how the individual fibrous layers 54 may be combined with a continuous stream of absorbent cores 28. The remaining steps for making an absorbent article such as a diaper are not further illustrated herein but are conventional steps as is known in the art, and include assembling the composite obtained with the other components of the absorbent article such as topsheet, backsheet and barrier leg cuffs. An example of absorbent article will be discussed below in relation with FIGS. 7-9.

In the present description, the reference numerals 54' and 52' refer to a continuous stream of not yet individualized distribution layer and acquisition layer respectively, while the numerals 54 and 52 refer to the corresponding individualized layers.

Airlaying Drum 100 and Molds 102

Figure 2:
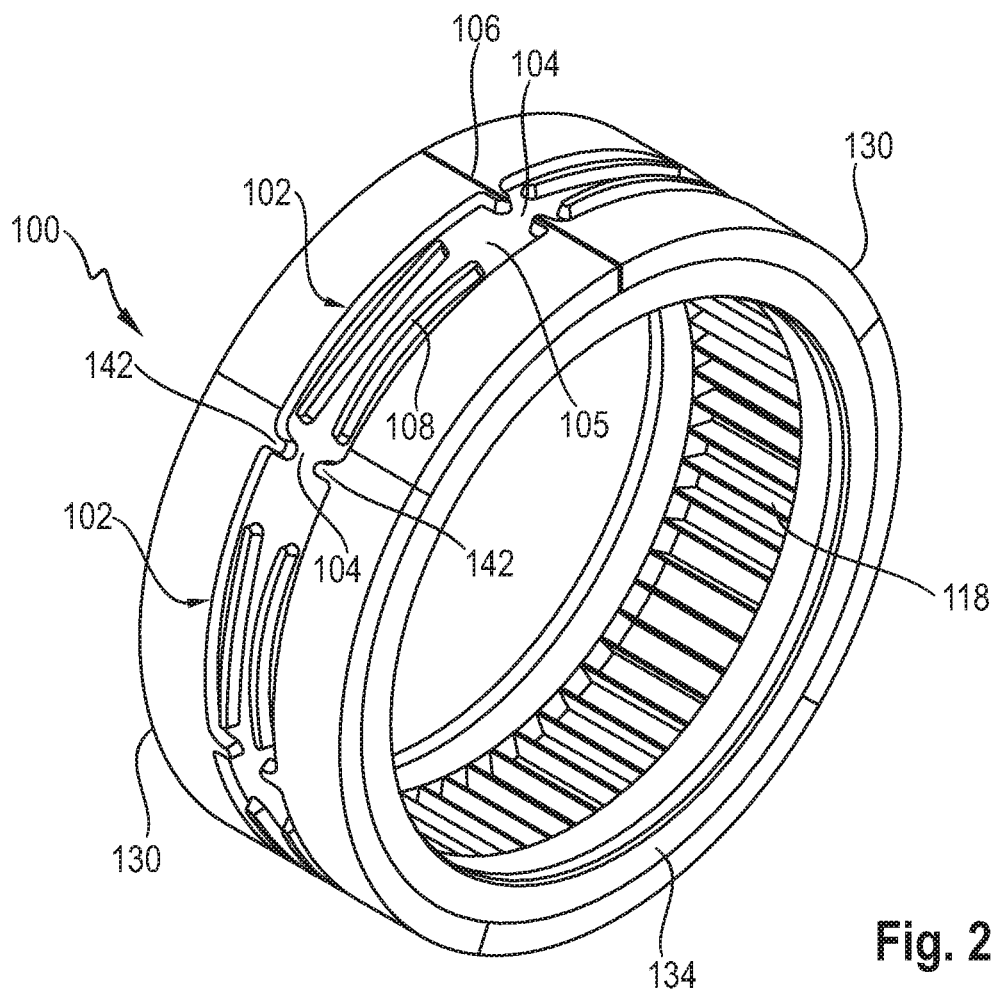
FIG. 2 shows a simplified perspective view of a fiber deposition drum that can be used in the present invention, the drum comprises several molds connected to each other by narrow connecting sections.
Figure 3:
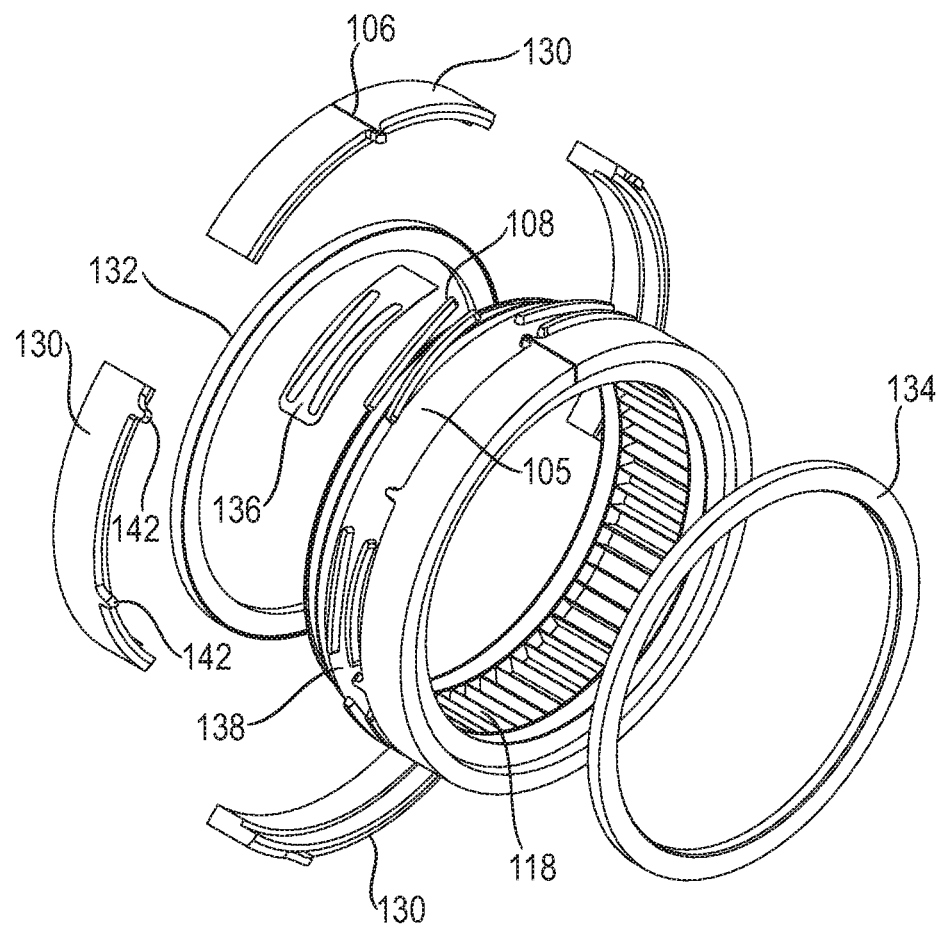
FIG. 3 shows an exploded view of the deposition drum of FIG. 2.

The airlaying drum 100 comprises a plurality of molds 102, which are shown in the more details in FIG. 2-3. The peripherical walls of the mold may be formed by a plurality of fences 130 which are attached on each side of the drum, as illustrated in FIG. 3. The fences 130, the outer rings 132, 134 and other drum components are typically made of metal and are attached to each other by screws in dedicated holes, which are not represented in Figures to simplify the views. Any two neighboring molds are connected by a connecting section 104, which has a different shape than the rest of the molds and thus can serve a cutting guide in the rest of the process. The connecting section 104 may typically be formed by two fingers 142 extending from the fences 130, thus providing for a shorter width at the connecting section relative to the width of the molds. The connecting section 104 and the fingers 142 are further illustrated on FIGS. 4-5. The molds are typically identical with another, including the position and shape of raised elements, so that they will be referred to as mold or molds in this description interchangeably, but it is also possible that one or more molds may be different than the others.

The molds are each provided with at least one raising element 108, for example a pair of raised elements as illustrated in the Figures. The shape and number of the raised elements in each mold can be varied depending of the type of the channels desired in the fibrous layer 54'. Illustrated are two discrete raised elements having a curvature similar to inverted brackets) (, but of course straight raised portions may also be used, or a single raised element having a simple or more complex shape, for example two raised elements that may be discrete or connected to each other, e.g. have a U- or V-shape etc. The plural form "raised elements" will be used further herein to mean "at least one raised element, in particular at least two raised elements", and the likewise "channels" will be used to mean "at least one channel, in particular at least two channels".

The raised elements 108 may be formed by attaching corresponding elements to the foraminous surface 105 of the drum 100. Unlike in the previously mentioned Venturino prior art, the raised elements of the invention are not part of the foraminous surface of the drum, so that no air flow communication exist between the raised elements and the negative pressure in the drum. The raised elements may be for example made of a resilient material such as a polyurethane rubber which may be glued to the foraminous surface 105 of the drum 100. A temporary metal mask 136 that fits exactly between the fences 130 on each side of the molds 102 may be used to position the raised elements within the mold's foraminous surface 105 when these are attached by gluing. This has the advantage that the glue cannot be applied accidently to the foraminous surface outside the area of the raised elements. Additionally, the raised elements can be attached to existing drums and/or can be easily replaced for maintenance or changing the shape of the raised elements if desired, by simply dissolving the glue.

The raised elements 108 prevent that a substantial amount of fibers is deposited on their top surface and side walls, thus creating areas within the fibrous layer that are substantially free of fibrous material. By "substantially free" it is meant that there may be a few fibers deposited on the raised elements due to accidental contamination but these are involuntary deposited. The raised elements are advantageously at least as high as the walls of the molds, which are formed by the fences on each side of the mold. The raised elements 108 preferably do not extend up to any of the walls of the drum, so that the resulting channels are completely encompassed within the individual fibrous layer 54'. Typically, the raised elements may be flush with the external walls of the molds. A scarfing unit 103 may be typically disposed directly after the molds 102 leave the forming chamber 101 to remove any excess fibers on the raised elements as well as in the rest of the molds 102. The fibers thus removed are then typically recycled and put back in the forming chamber, as is known in the art and thus not herein further detailed.

The airlaying forming drum comprises a foraminous surface 105, which is typically a thin metal plate having very fine pores that let air through but no fibers, and which is connected to a negative pressure (vacuum) inside the drum. The fibers 70 introduced in the forming chamber 101 are drawn into the surface of the molds 102, except of course for the raised elements that are not connected to the negative pressure. The foraminous surface of the drum is typically itself provided as a plurality of members which are connected end to end to form a cylinder around the drum periphery. A supporting frame is typically likewise provided under the foraminous surface, typically referred to as a honey comb due to the presence of many regularly disposed holes (not shown) and another support layer underneath may comprise a plurality of thin elongated rims 118 as illustrated in FIGS. 2-3, that provide structure integrity to the drum while providing a good air flow connection between the negative pressure inside the drum and the external surface of the drum. Two outer rings 132, 134 may be provided to fix the fences 150 with the supporting inner frame, as is known in the art (typically by metal screw attachments, not shown in the Figures for simplification). The drum 100 may also comprise an optional homing line 106 which may be aligned with one of the connecting section. Such homing line may be etched in the metal fences and may be further colored to be easily recognizable by the operator of the production line. The homing line 106 may be aligned with the desired cut line 150 of a connecting section 104. The operator can use the homing line to register the different apparatus such as the cutting unit 114 and the other layers such as the absorbent core 28 before starting the line to ensure that these are registered. Of course, other constructions are possible without departing from the invention. The first endless moving surface used for the depositing the fibers may even not need a drum, as it could be for example an endless forming belt, such as for example shown in U.S. Pat. No. 5,466,409 (Partridge et al.).

The connecting sections 104 and the foraminous surface 105 of the molds may have the same depth relative to the peripheral walls of the molds and the raised elements, but the depth may also be varied if it desired to provide the fibrous layer with a varying thickness, for example having less fibers on the side of the fibrous layer 54' that will be oriented towards the back of the article. The mold's foraminous surface 105 may also have a constant depth and the connecting sections 104 have a different, e.g. smaller depth, so that less fibers are deposited in the connecting sections relative to the rest of the fibrous layer, excluding of course the raised elements 108.

Unmolding and Cutting

As indicated previously, two neighboring molds 102 on the forming drum 100 are connected to each other by a connecting section 104, which typically has a narrower width W1 than the molds W2. In this way, a continuous layer 54' of fibrous material is formed and can be deposited in the forming drum 100, unlike for example in WO2017/189188 where each mold is not connected to the neighboring molds. After the (optional) scarfing unit 103 is passed, this continuous fibrous material is transferred from the forming drum to a second endless surface, which may be for example a conveyor belt 110, as represented. The inventors have found that such a continuous layer 54' is easier to transfer reliable out of the forming drum onto the conveyor 110. Of course, the unmolding of the continuous fibrous layer 54' is helped by removing the negative pressure at the exit point or even switching to a positive pressure wherein the first and second endless moving surface meet.

The channels 86 have the generally same shape as the raised elements 108 in the molds according to the general shape and position of which they were formed. The channels and the raised elements are typically disposed symmetrically relative to the longitudinal axis of the article 80 and of the fibrous layer 54. The channels 86 may be thus have any desired shapes and positions. There may be for example only one discrete channel, for example having a U or V shape comprising two branches which meet at one extremity, or having a O shape with both extremities connected, or a X shape, or Y shape etc. The channels may be straight, including parallel to the longitudinal axis and/or angled relative to the longitudinal axis, or the channels may be curved, or a combination of both straight and curved, etc. The channels may have a minimum width of for example at least 2 mm, or at least 4 mm and a maximum width of for example up to 20 mm, or up to 12 mm. A typical width may be from 6 to 8 mm. Of course, the channel's width may vary along the channels, the value indicated may thus be measured in at least one channel section having length of at least 20 mm. The channels may have any length, for example from 50 mm to 400 mm, as measured projected along the longitudinal axis 80. It is also possible to have channels formed by a plurality of shorter segments separated by buffer zones. The channels may be typically longitudinally oriented, that is at least twice longer in the longitudinal direction than in the transversal direction. The channels 86 may also advantageously not extend to the edges of the fibrous layer 54 but remain fully encompassed with the fibrous layer.

The continuous fibrous layer 54' can optionally be transferred on a support layer 52'. The support layer 52' can be provided as a continuous stream on the second moving endless surface 110, as represented in FIG. 1. Such a support layer may typically be a nonwoven layer comprising synthetic fibers. The support layer may later serve as an acquisition layer 52 in a finished absorbent article 20, and exemplary materials are disclosed in more details further below. Glue may be typically applied on the support layer, as represented by the glue applicator 112, for example as a series of glue slots or spiral glue, as is known in the art. This helps fixing the fibrous layer 54' to the support layer 52'. The second endless moving surface 110 moves the laminate of the two layers at a certain speed towards the cutting unit 114.

The cutting unit 114 comprise a knife that cuts the continuous fibrous layer 54' precisely along a cut line 150, which may be targeted to be in the middle of the area of the fibrous continuous layer corresponding to the connecting section 104. The homing line 106 may be used to facilitate registration so that the blade of the cutting knife cuts precisely the fibrous layer 54' at the desired position in the connecting section, even at the high production speed used in diaper manufacturing. The cutting unit 114 cuts simultaneously the support layer 52', when such layer is present, and the fibrous layer 54'.

Figure 4:
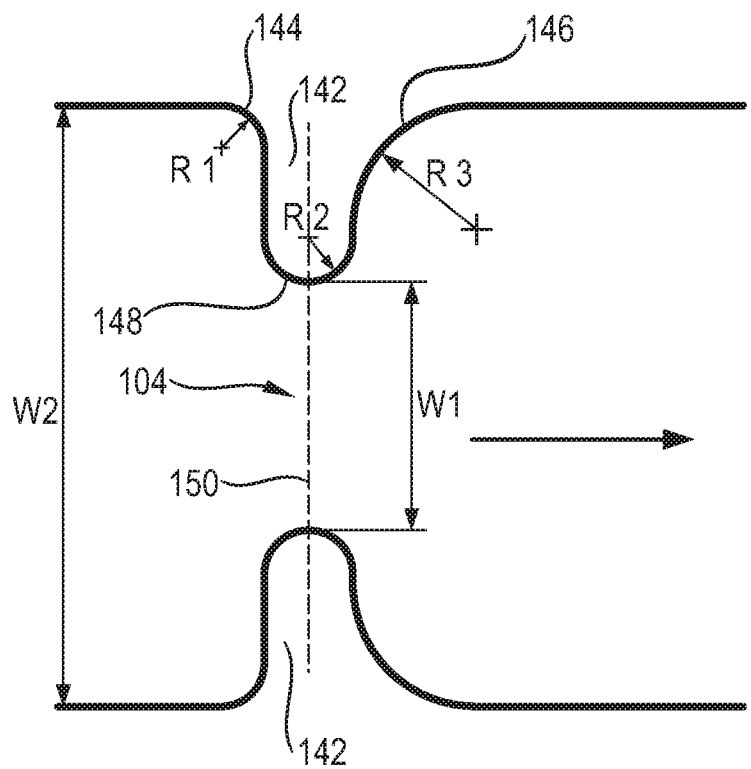
FIG. 4 shows a close-up view of a pair of fingers which forms a connecting section.
Figure 5:
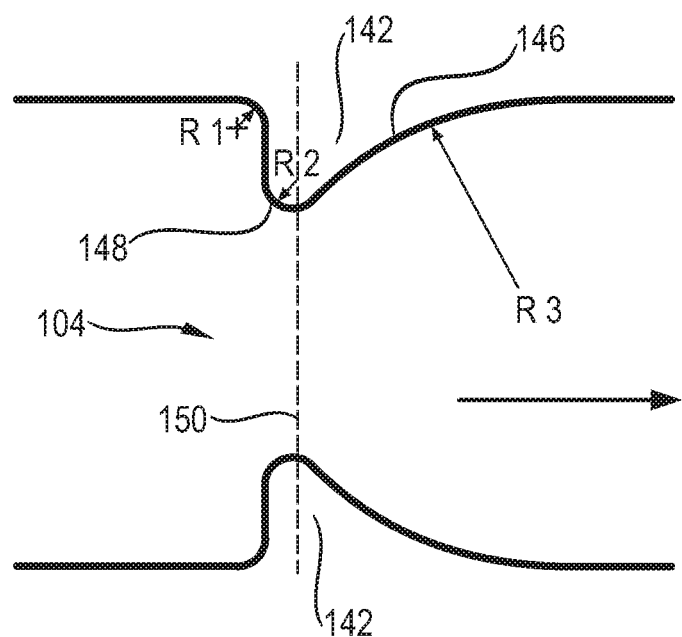
FIG. 5 shows an alternative finger shape.

FIG. 4 and FIG. 5 illustrate two exemplary configurations for the connecting sections, with the target cutting line 150 shown in broken lines. The machine direction for the continuous fibrous layer 54' is shown by the arrow pointing to the right. The connecting sections 104 have a smallest width W1 defined by the distance between the two fingers 142. The molds have a maximum width W2. The width W1 may represent from 20% to 80% of the width W2, in particular from 25% to 60% of the width W2. The width W2 may be typically constant along the length of the mold, but the width of the mold may also vary to make shaped fibrous layer, in the latter case the maximum width of the mold W2 is reported. The fingers 142 are advantageously sufficiently short and thick so that they extend from the fences 130 without the need for additional attachment features. This allows using a conventional forming drum without modification to the foraminous surface 105 and the underlying support structure.

The fingers are each defined at their base by two corners 144, 146. As shown in FIG. 4, the right base corner 146 of the connecting section 104 corresponds to the trailing edge of the not-yet individualized fibrous layer and the left side corner 144 to the leading edge of the following next fibrous layer. The two corners 144, 146 forming the base of each finger 142 may extend a right angle from the edges of the mold, but preferably these corners are rounded. It was found that rounded corners provide a more repeatable fibers deposition comparative to straight corners. The curvature of first rounded corner 146 may be the same of different than the curvature of the second rounded corner 144. For example, the radius of curvature R1 of one corner of the finger may be smaller than the radius of curvature R3 of the other corner of the finger. This difference of curvatures is shown in a more exaggerated form in FIG. 5, with the corner 146 on the leading edge of the connecting section having a much larger radius of curvature R3 than the radius of curvature R1 on the trailing edge. Having different curvatures on either side provides a different profile of the front and back edges of the fibrous layer. For example, it may be preferred that the back edge of the fibrous layer comprise less fibrous material than the front edge of the fibrous layer, when the fibrous layer is incorporated in a finished article. The tip 148 of each finger may also be rounded to provide for a better deposition, with a curvature radius (R2)

As another advantage of having a connecting section comprising fibrous material, it was found that the knife cutting through the support layer/fibrous material wears less quickly than if no fibers were present. Additionally, the fibers help removing any excess glue that has been applied to the support layer by the glue applicator 112 that may otherwise contaminate the blade.

Assembling with Additional Components

Figure 6:
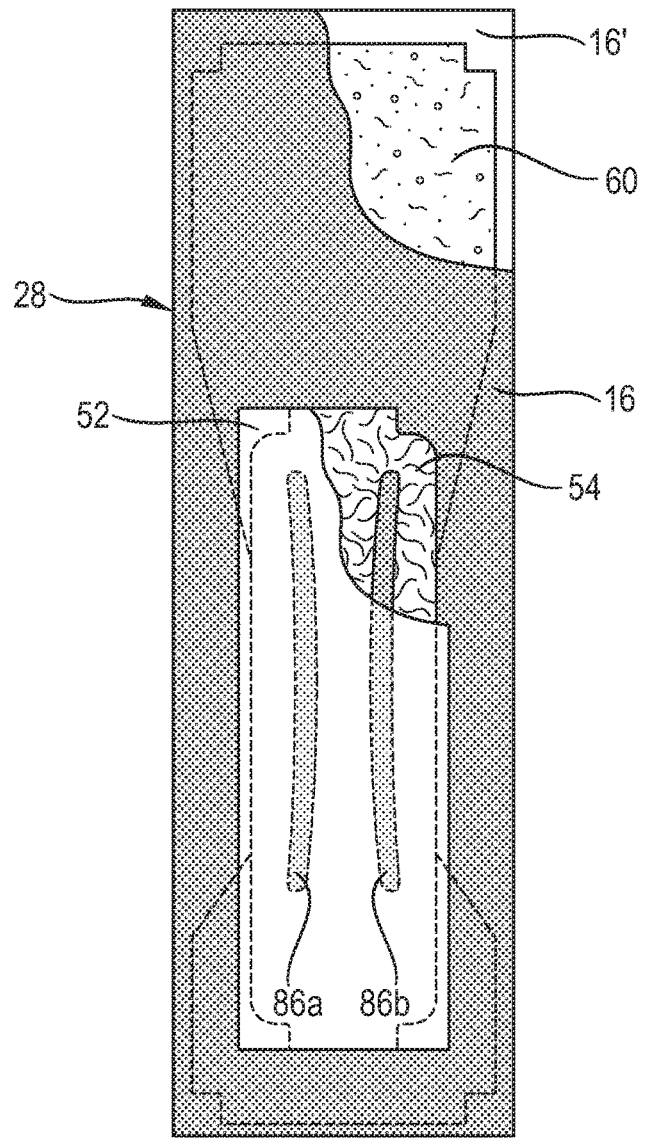
FIG. 6 shows the combination of an acquisition layer, a distribution layer and absorbent core, the distribution layer being a fibrous layer obtained by the process described herein.

The individualized fibrous layer 54, whether on a support layer 52 or not, can be transferred after the cutting step to a third endless moving surface such as a conveyor belt 120 for assembling with further components. This third endless moving surface typically moves at a higher speed than the second endless moving surface so that the individualized fibrous layers 54 are automatically spaced relative to each other. In the example illustrated in FIG. 1, a continuous stream of not-yet individualized absorbent cores 28 is provided. The stream of absorbent cores 28 typically comprise a continuous supply of absorbent material layers sandwiched between a core wrap, with two neighboring absorbent layers separated from each other by a gap free of absorbent material. An optional glue applicator 116 may apply glue on one side of the core wrap of the continuous absorbent core stream, the glue may be slot coated or sprayed as is known in the art. This side of the absorbent core stream may then be contacted directly or indirectly against the individual fibrous layers. Again, registration is important so that the fibrous layer (optionally with support layer) is married with the absorbent core at the desired position. The continuous stream of absorbent cores is then cut in cross-machine direction where the absorbent layer is not present, where only the core wrap is present. An example of the composite obtained is illustrated in FIG. 6, showing an exemplary absorbent core 28 having a shaped absorbent layer 60 disposed underneath the support layer 52/fibrous layer 54 laminate discussed before. As indicated, the support layer may serve as an acquisition layer 52 and the fibrous layer as a distribution layer 54.

Figure 7:
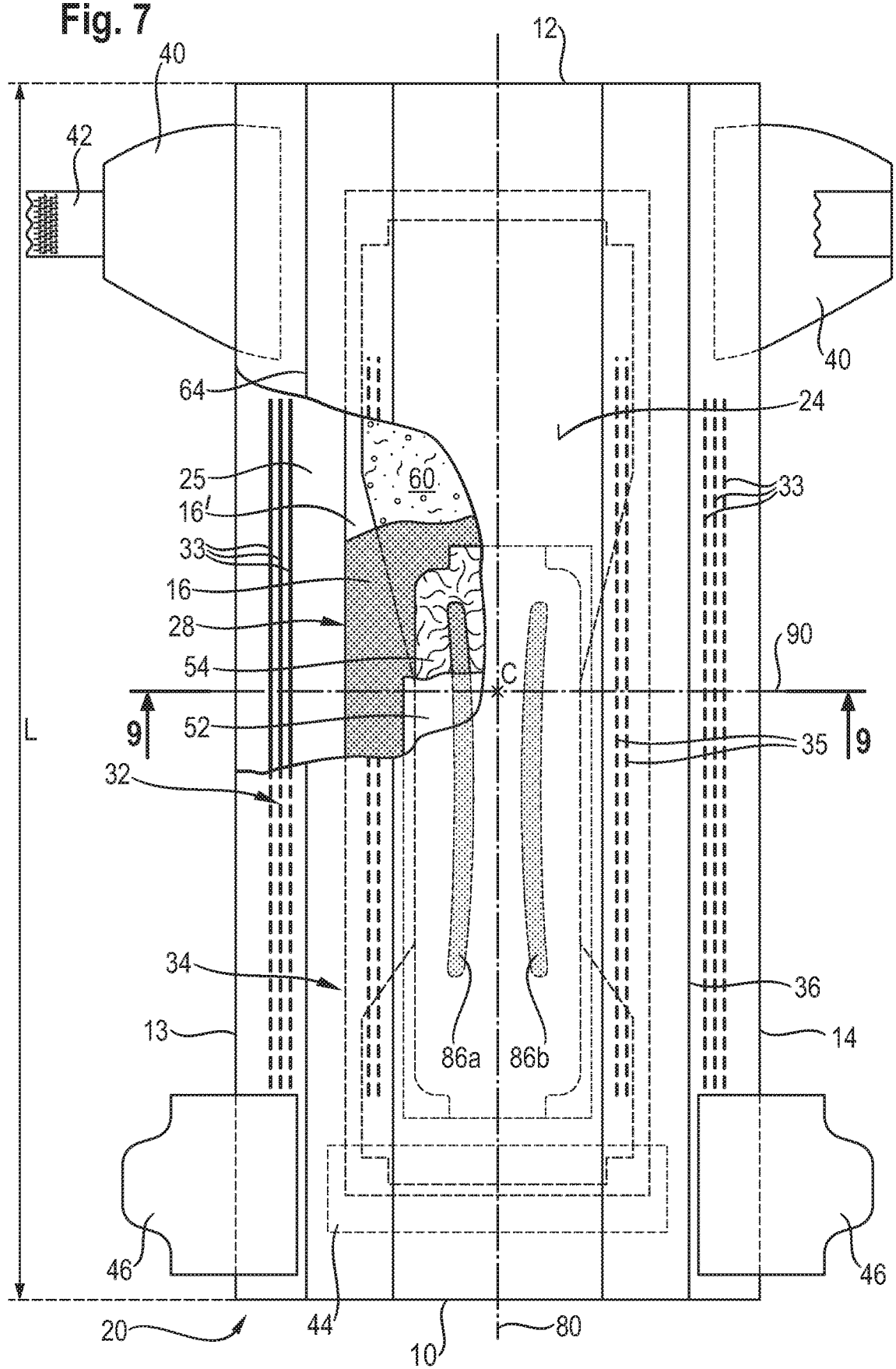
FIG. 7 shows an exemplary diaper incorporating the composite structure of FIG. 6, with some layers partially removed to show the distribution of the inner layers of the diaper.
Figure 8:
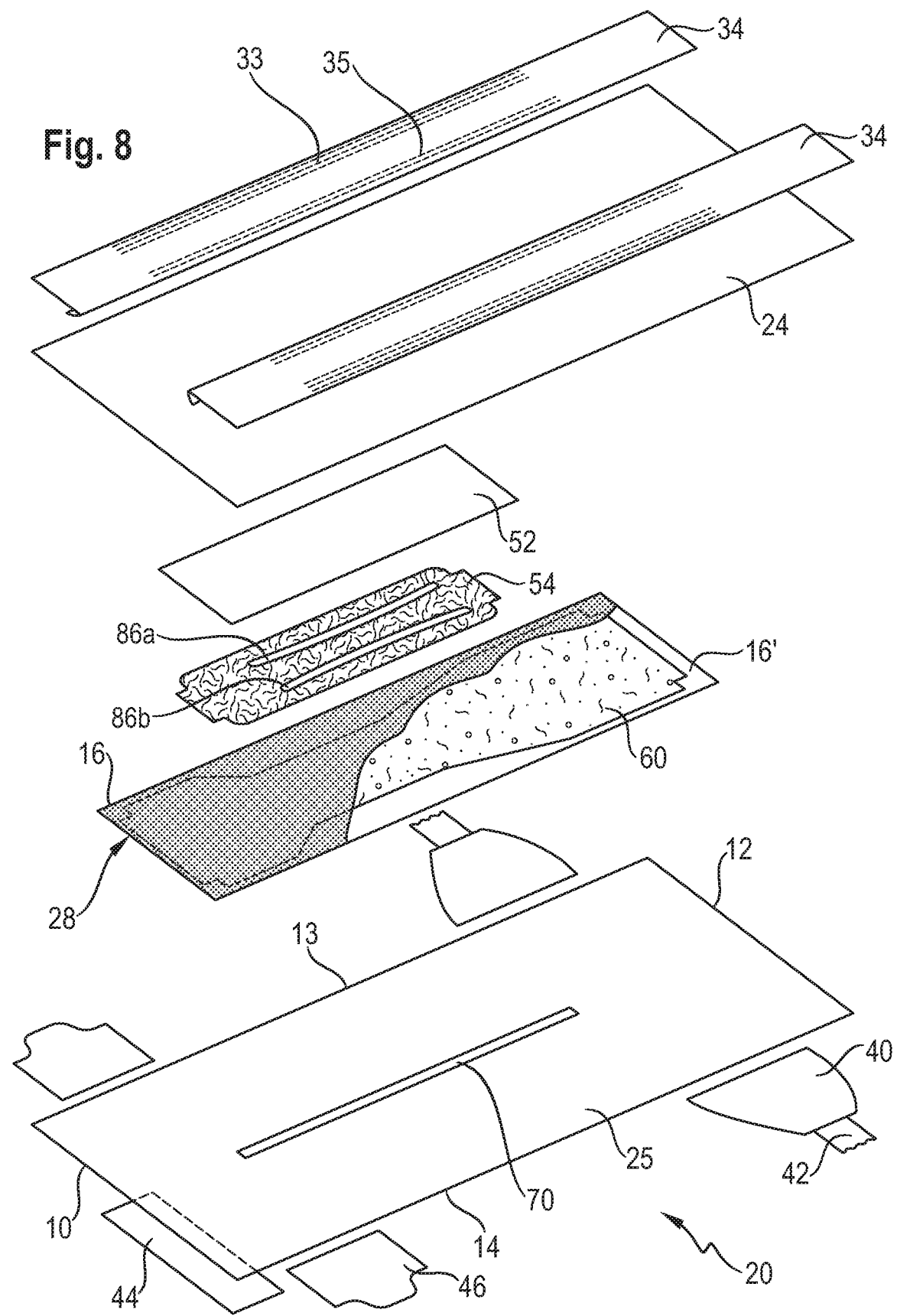
FIG. 8 shows an exploded view of the diaper of FIG. 7.
Figure 9:
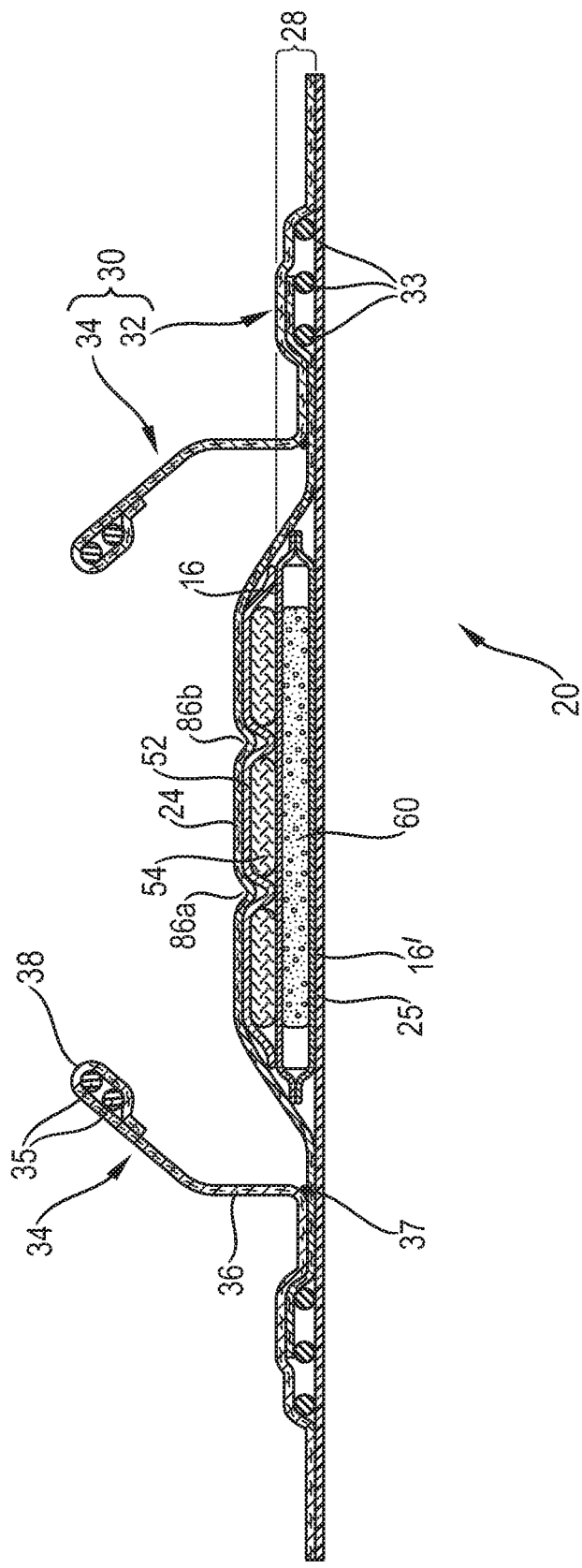
FIG. 9 shows a transversal cross-section of the taped diaper of FIG. 7.

Further layer components of an absorbent articles are then further added in a conventional manner, the process of which is not represented herein, with an exemplary diaper shown in FIGS. 7-9 discussed hereafter.

Alternatives

While not represented in the Figures, several alternatives are possible while remaining in the scope of the invention. For example, the continuous support layer 54' (or another web as support layer) may be fed on the forming drum before the forming chamber 101 so that it is pressed against the forming drum by the negative pressure. The fibers are then directly deposited on the support layer while it is maintained on the deposition drum 100. In another alternative, it would also be possible to provide the continuous stream of absorbent cores 28 as a support layer instead of the acquisition layer 54. In another alternative, the support layer may be a topsheet 24 instead of an acquisition layer.

General Description of an Absorbent Article 20

An exemplary absorbent article according to the invention in the form of a baby taped diaper 20 is represented in FIGS. 7-9. FIG. 7 is a top plan view of the wearer-facing side of an exemplary diaper in a flat-out state, with portions of the structure being cut-away to more clearly show the construction of the diaper. This diaper 20 is shown for illustration purpose only, as the invention may be used for making a wide variety of diapers or other absorbent articles such as pant-like diapers, training pants, adult incontinence pants or feminine sanitary pads. In the following description the term diaper and absorbent article are used interchangeably.

As illustrated in FIG. 7, the absorbent article 20 comprises a front edge 10, a back edge 12, and two longitudinally-extending side (lateral) edges 13, 14. The front edge 10 is the edge of the article which is intended to be placed towards the front of the user when worn, and the back edge 12 is the opposite edge. The absorbent article is notionally divided by a longitudinal axis 80 extending along a longitudinal direction from the middle of the front edge to the middle of the back edge of the article and dividing the article in two substantially symmetrical halves relative to this axis, when viewing the article from the wearer-facing side in a flat-out configuration, as exemplarily shown in FIG. 7. If some parts of the article are under tension due to elasticized components, the article may be typically flattened using clamps along the periphery of the article and/or a sticky surface, so that the article can be pulled taut so as to be substantially flat. Closed articles such as pant-like baby diapers, training pants for small children, or adult incontinent pants may be cut open along the side seams to apply them on a flat surface, as is known in the art. Unless otherwise indicated, dimensions and areas disclosed herein apply to the article in this flat-out configuration.

The article has further a length L as measured along the longitudinal axis 80 from the back edge 12 to the front edge 10. The absorbent article can also be notionally divided by a transversal axis 90 at half the length L. The transversal axis 90 is perpendicular to the longitudinal axis 80 and placed at half the length of the article. The intersection of the longitudinal axis 80 and the transversal axis 90 is defined herein as the centerpoint C of the article. The article can be further notionally divided in three regions having equal length of a third of L along the longitudinal axis: a front region extending from the front edge 10 towards the crotch region for a third of L, a crotch region in the middle third of the diaper, and a back region extending from the crotch region to the back edge 12 of the article for the remaining third of L. All three regions are of equal length measured on the longitudinal axis, when the article is in such a flat state. The front region, crotch region, back region and longitudinal and transversal axis are defined herein notionally, that is they are typically not materialized in the real diapers, but are useful to describe the positions of various components of the invention relative to each other and the diaper.

The absorbent article 20 comprises a liquid-permeable topsheet 24, a liquid-impermeable backsheet 25 and an absorbent core 28 between the topsheet and the backsheet. The absorbent core comprises an absorbent material 60 enclosed in a core wrap having a top side 16 and bottom side 16'. The absorbent material 60 defines an absorbent layer having a deposition area within the core wrap.

Distribution and Acquisition Layers 52, 54

The absorbent article further comprises one or more intermediate layers between the topsheet and the absorbent core. The fibrous layer obtained according to the process described above may be used as such an intermediate layer, referred to herein as distribution layer 54. The distribution layer 54 is advantageously made of a distribution or acquisition layer material to provide fluid-handling properties. The distribution layer can advantageously spread an insulting fluid over a larger surface within the article so that the absorbent capacity of the core can be more efficiently used. Such a distribution layer may be smaller in surface than the absorbent material layer and typically does not extend beyond the edges of the absorbent layer. Distribution layer and acquisition layer are typically free of superabsorbent polymers.

A typical example of such material comprises or consists of cross-linked cellulose fibers. The masking layer may for example comprise at least 50% by weight of cross-linked cellulose fibers. The cross-linked cellulosic fibers may be crimped, twisted, or curled, or a combination thereof including crimped, twisted, and curled. The distribution layer may advantageously have a relatively high basis weight, for example an average basis weight of at least 50 g/m$^2$, in particular from 50 g/m$^2$ to 300 g/m$^2$, and advantageously of at least 100 g/m$^2$. The average basis weight is calculated by dividing the weight amount of the fibers by the area of the distribution layer where the fibers are present (including the channels). The density of the layer may vary depending on the compression of the article, but may typically range from 0.03 g/cm$^3$ to 0.25 g/cm$^3$, in particular from 0.05 g/cm$^3$ to 0.15 g/cm$^3$, measured at 0.30 psi (2.07 kPa). The density of the intermediate layer is measured at the centerpoint C of the article for this purpose.

The acquisition layer material is typically a nonwoven material. As used herein, the terms "nonwoven material", "nonwoven layer", "nonwoven web" or more simply "nonwoven" are defined as a sheet of fibers, continuous filaments, or chopped yarns of any nature or origin, that have been formed into a web by any means, and bonded together by any means, with the exception of weaving or knitting (ISO 9092 definition). Felts obtained by wet milling are not nonwovens. The fibers may be of natural or synthetic origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter (g/m$^2$ or gsm).

Nonwovens have the advantage that they can be manufactured outside the converting line and stored and used as a roll of material. A typical acquisition layer that may be used in the present invention is a bonded carded web, a through-air bonded carded web ("TABCW"). The acquisition material layer may also be a latex bonded nonwoven. An alternative acquisition material may for example be a SMS (spunmelt) nonwoven material.

General Description of an Absorbent Core 28

The absorbent core 28 is the component of the article that has the maximum fluid retention capacity. The absorbent core comprises an absorbent material 60 that is typically contained in a core wrap 16, 16'. Various constructions are possible. As used herein, the term "absorbent core" does not include the topsheet, the backsheet or a distribution/acquisition layer. The absorbent core comprises all or at least the majority of superabsorbent polymer (SAP) in the article. The core typically thus consists essentially of, or consists of, the core wrap, the absorbent material and optionally construction adhesives. The absorbent material may consist of a blend of SAP particles and cellulose fibers, but the invention is also applicable to other absorbent material for example consisting to 100% of SAP particles. The terms "absorbent core" and "core" are herein used interchangeably.

The absorbent material 60 may be any conventional absorbent material used in absorbent articles. The absorbent material usually comprises superabsorbent polymers (SAP) as is known in the art. The SAP is typically distributed in the form of small particles, which may be distributed in a matrix of cellulose fibers in so-called airfelt cores. The SAP typically represents from 40% to 80% of the weight of the absorbent material, the rest being cellulose and/or synthetic fibers. More recently, so called pulp-less or airfelt-free absorbent cores have been put on the market, wherein the absorbent material does not comprise cellulose fibers.

Suitable SAP may be any water-insoluble, water-swellable polymers capable of absorbing large quantities of fluids, as is known in the art. The term "superabsorbent polymer" refers herein to absorbent materials, typically cross-linked polymeric materials, that can absorb at least 10 times their weight of an aqueous 0.9% saline solution as measured using the Centrifuge Retention Capacity (CRC) test (EDANA method WSP 241.2.R3 (12)). The SAP may in particular have a CRC value of more than 20 g/g, or more than 24 g/g, or of from 20 to 50 g/g, or from 20 to 40 g/g, or 24 to 30 g/g.

The core wrap may be typically comprised of one sheet of core wrap material folded over the absorbent material or alternatively from two sheets of core wrap material forming respectively a top side and a bottom side of the core wrap, with suitable attachment along the longitudinal edges and optionally the front and back edges. The core wrap material is typically a low basis weight nonwoven (12 gsm or less). The top side of the core wrap may be treated to be more hydrophilic than the bottom side.

The core wrap material may be any materials suitable for receiving and containing the absorbent material. Typical substrate materials used in the production of conventional cores may be used, in particular paper, tissues, films, wovens or nonwovens, or laminate of any of these. The core wrap may in particular be formed by a nonwoven web, such as a carded nonwoven, spunbond nonwoven ("S") or meltblown nonwoven ("M"), and laminates of any of these. For example, spunmelt polypropylene nonwovens are suitable, in particular those having a laminate web SMS, or SMMS, or SSMMS, structure, and having a basis weight range of about 5 gsm to 15 gsm.

The core wrap 16 may optionally have a visible appearance that contrasts with the rest of the article, in particular with the appearance of the fibrous layer 54. For example, the top side of the core wrap may be treated or manufactured to have a color (e.g. any shades of green, blue, yellow, brown, grey, red etc.) while the masking layer is generally untreated so that it retains a generally white appearance (as is common for cellulosic fibers or non-colored plastics) or as a different color. An example of contrasting layer 16 is a nonwoven layer made of synthetic fibers which have been colored by the addition of a pigment during its manufacture. The contrasting layer is at least partially visible on the wearer-facing surface of the article through the see-through areas and thus can provide a visual signal highlighting the presence and position of the channels 86, which may be three-dimensional channels, as indicated above. Typical topsheets (and optionally present acquisition layers) have a low basis weight and are translucent so that the contrasting layer is visible through these layers.

Color may be imparted to a contrasting layer by way of impregnation of a colorant into the substrate material. Colorants such as dyes, pigments, or combinations may be impregnated in the formation of substrates such as polymerics, resins, or nonwovens. For example, the colorant may be added to molten batch of polymer during film, fiber, or filament formation. EP2,886,093A1 (Kreuzer et al.) discloses various ways to provide color or another contrasting means to a nonwoven layer, which are also applicable herein to make the contrasting layer, and in particular includes adding a pigment in a synthetic uncolored material which is then manufactured in a nonwoven (compounding or masterbatching). Other applicable contrasting methods are also included such as printing or coating a contrasting layer on whole of the contrasting layer or on selected areas corresponding to the see-through areas.

The absorbent material 60 defines an absorbent material deposition area within the core wrap. The deposition area is delimited by the periphery of the absorbent layer formed by the absorbent material, as seen from above within the plane of the core. The deposition area may be generally rectangular as shown in the Figure, but it may also be advantageously shaped so that the longitudinal edges of the cores have a tapered section in the crotch region relative to the front region and/or back region, as is known in the art for so-called "shaped cores". Small size baby diapers may also comprise a notch on the front edge of the absorbent material's deposition area to adapt to the presence of remains of the umbilical cord of very small babies.

The absorbent cores may also comprise macroscopic channels, which are absorbent material free areas encompassed within the deposition area. The top side and the bottom side of the core wrap may be bonded to each other through these channel areas. Absorbent cores having such channels are for example disclosed in WO2012/170778A1, Rosati et al., or WO 2014/200794 A1, Bianchi et al. If such core channels are present, the channels 86a, 86b in the distribution layer may be partially or completely aligned with these. On the other hand, the absorbent core may also advantageously not comprise channels or these may be not aligned with the channels 86 in the fibrous layer, as these channels 86 already provide fluid transport and distribution, and having core without channels may provide more absorbency in the absorbent core.

The absorbent cores of the present invention may be made by any conventional or known processes. The absorbent cores may be conventionally made by air-laying a mix of cellulose fibers and superabsorbent particles on a conventional air-laying drum. Raised elements matching the shapes of the desired channels so that that substantially no absorbent material is deposited in these areas may be used. See for example WO2004/011723 (Venturino et al.) for a modified drum having raised elements to create areas having different basis weight. The shape of the raised elements may be adapted to make any desired channel shapes.

The absorbent core may have any caliper. Typically, the caliper of the core (dry, i.e. before use) as measured at the centerpoint point (C) or at any other points of the surface of the core according may range from 2.0 mm to 10.0 mm, in particular from 3.0 mm to 7.0 mm as measured at 2.07 kPa (0.30 psi) with a flat circular foot having a diameter of 17.0 mm (±0.2 mm).

Topsheet 24

The topsheet typically forms most of the wearer-contacting surface of the article and is the first layer that the body exudates contact. The topsheet is preferably compliant, soft-feeling, and non-irritating to the wearer's skin. Further, at least a portion of the topsheet is liquid permeable, permitting liquids to readily penetrate through its thickness. Any known topsheet may be used in the present invention. A suitable topsheet may be manufactured from a wide range of materials. Most topsheets are nonwoven materials or apertured formed films, but other materials are possible such as porous foams, reticulated foams, woven materials. Typical diaper topsheets have a basis weight of from about 10 gsm to about 28 gsm, in particular from about 12 gsm to about 18 gsm but higher basis weights are possible if it is desired to provide a very soft feeling wearer-contacting surface for example.

As illustrated in FIG. 9, the topsheet 24 may directly or indirectly (e.g. together with an acquisition layer 52) be bonded through the channels to an underlying layer, e.g. an absorbent core. The topsheet may be attached for example by gluing or other known attachment techniques such as heat bonding and/or pressure bonding Backsheet 25

The backsheet may be any backsheet known in the art for absorbent articles. The backsheet may be positioned directly adjacent the garment-facing surface of the absorbent core. The backsheet prevents, or at least inhibits, the exudates absorbed and contained therein from soiling articles such as bedsheets and undergarments. The backsheet is typically impermeable, or at least substantially impermeable, to liquids (e.g., urine). The backsheet may, for example, be or comprise a thin plastic film such as a thermoplastic film having a thickness of about 0.012 mm to about 0.051 mm.

The basis weight of those films is usually as low as possible to save material costs, typically from 10 gsm to 30 gsm, in particular below 20 gsm. A covering low basis weight nonwoven may be attached to the external surface of the film to provide for a softer touch.

Fastening System 42, 44

The absorbent article may include a fastening system, especially when the article is a taped diaper as exemplified in FIG. 1. The fastening system can be used to provide lateral tensions about the circumference of the absorbent article to hold the absorbent article on the wearer. Such a fastening system is not necessary for pant articles such as training pants and adult incontinence pants since the waist region of these articles is already bonded and elasticized. The fastening system usually comprises a fastener 42 such as tape tabs, hook and loop fastening components, interlocking fasteners such as tabs & slots, buckles, buttons, snaps, and/or hermaphroditic fastening components, although any other known fastening means are generally acceptable. A landing zone 44 is normally provided on the front waist region of the article for the fastener 42 to be releasably attached.

The absorbent article may comprise front ears 46 and back ears 40 as is known in the art in taped diapers. Absorbent articles in pant chassis are already sealed along the waist edges typically do not require front ears and back ears. The ears can be integral part of the chassis, for example formed from the topsheet and/or backsheet as side panel. Alternatively, as represented in FIG. 1, they may be separate elements attached by gluing and/or heat embossing. The back ears 40 are optionally stretchable to facilitate the attachment of the tabs 42 on the landing zone 44 and maintain the taped diapers in place around the wearer's waist. The front ears 46 may also be optionally elastic or extensible to provide a more comfortable and contouring fit.

Barrier Leg Cuffs 34 and Gasketing Cuffs 32

Absorbent articles such as taped diapers, training pants or adult incontinence pants may typically further comprise cuff components 30 that improve the fit of the article around the legs of the wearer. Such cuffs typically comprise barrier leg cuffs 34 and gasketing cuffs 32. The cuffs 30 may comprise a piece of material, typically a nonwoven, which is one side partially bonded to the article and on the other side can be partially raised away from the topsheet and thus stand up from the plane defined by the topsheet as shown for example in FIG. 9. Both parts of the cuffs may be advantageously elasticized. The raised part of the cuff components is referred to herein as barrier leg cuffs 34 and can provide improved containment of liquids and other body exudates approximately at the junction of the torso and legs of the wearer. The barrier leg cuffs 34 extend at least partially between the front edge and the back edge of the absorbent article on opposite sides of the longitudinal axis and are at least present adjacent to the center point C of the article.

The barrier leg cuffs 34 may be delimited by a proximal edge 37 joined to the rest of the article, typically the topsheet, and a free terminal edge 38 intended to contact and form a seal with the wearer's skin. The barrier leg cuffs 34 may be joined at the proximal edge 37 with the chassis of the article by a bond which may be made for example by adhesive bonding, fusion bonding or combination of known bonding means, for example as disclosed in WO2014/168810A1 (Bianchi et al.). The bond at the proximal edge 37 may be continuous or intermittent.

The barrier leg cuffs 34 can be integral with (i.e. formed from) the topsheet or the backsheet, or more typically be formed from a separate material joined to the rest of the article. Typically, the material of the barrier leg cuffs may extend through the whole length of the article but is "tack bonded" to the topsheet towards the front edge and back edge of the article so that in these sections the barrier leg cuff material remains flush with the topsheet. Each barrier leg cuff 34 may comprise one, two or more elastic strings 35 close to its free terminal edge 38 to provide a better seal.

In addition to the barrier leg cuffs 34, the article may comprise gasketing cuffs 32, which are formed in the same plane as the chassis of the absorbent article, in particular may be at least partially enclosed between the topsheet and the backsheet, and typically placed further laterally outwardly relative to the barrier leg cuffs 34. The gasketing cuffs 32 can provide a better seal around the thighs of the wearer. Usually each gasketing leg cuff 32 will comprise one or more elastic string or elastic element 33 comprised in the chassis of the diaper, for example between the topsheet and backsheet in the area of the leg openings. Typically, the barrier leg cuffs 34 are disposed more internally than the gasketing cuffs 32. The barrier leg cuffs are thus also referred to as inner cuffs and the gasketing cuffs as outer cuffs.

Other Components

The absorbent articles of the invention can further comprise any other typical components known for the intended purpose of the article that are not illustrated in the Figures, such as a transverse barrier element extending across the topsheet to form a receptacle for bowel movement, a lotion application on the topsheet, a wetness indicator comprising a pH indicator disposed between the absorbent core and the backsheet, etc. These components are well-known in the art and will not be further discussed herein. Reference is made to WO2014/093310 where several examples of these components are disclosed in more details.

The absorbent article may also comprise an elastic waist band (also called elastic waist feature) disposed parallel to and along the back edge of the article and/or less commonly parallel to and along the front edge of the article. Such waistbands help providing improved fit and containment at the back and/or front edge of the article. The elastic waist feature is generally intended to elastically expand and contract to dynamically fit the wearer's waist. The elastic waistband may be constructed in a number of different configurations. Non-limiting examples of back and front waistbands can be found in WO2012/177400 and WO2012/177401 (Lawson), and U.S. Pat. Nos. 4,515,595, 4,710,189, 5,221,274 and 6,336,922 (VanGompel et al.). Pant-like articles As indicated previously, the invention may be also used in absorbent articles presented in the form of a pant or underwear (herein "pant"). In these articles, the waist and the leg openings are pre-formed during manufacture so that the article can be put on like underwear. These pant articles typically have a front waist panel and a back waist panel which are sealed together via side seams. The side seams can be broken to remove and discard the article and are typically not re-fastenable. The front and back waist panels are typically elasticized. Pants can be used as taped diapers on babies and younger children for day wear and for overnight dryness, as training pant for older children at the toilet training stage, and also as adult incontinence protection.

Pant-like articles typically comprise a front waist panel and a back waist panel joined together via side seams to form the waist opening and at least part of the leg openings. The waist panels are typically elasticized, either using a material which is inherently elastic to make them (such as a laminate comprising an elastomeric layer between two nonwoven layers) or by sandwiching a plurality of elastic strands between two nonwovens along the width of the panels, as is known in the art. Pants also typically comprise a chassis comprising the remaining components of the article, in particular the topsheet, the backsheet, the absorbent core and barrier cuffs including upstanding barrier leg cuffs and attached on one side to the front waist panel and on the other side of the back waist panel. These components may be generally constructed as in previously disclosed for the taped diaper.

Packages

A plurality of articles comprising the fibrous layer 54 obtained by the process disclosed therein may be typically packaged in a package for transport and sale. At least 50% of the articles, and preferably all the articles, in the package may be according to the invention. The articles may be folded and packaged as is known in the art. The package may be for example a plastic bag or a cardboard box. Diapers may typically be bi-folded along the transversal axis and the ears folded inwardly before being packaged. The absorbent articles may be packed under compression so as to reduce the size of the packages, while still providing an adequate number of absorbent articles per package. It was also found that pressure can help maintaining the different layers on close contact until the bag is opened. This is beneficial for allowing the glue to achieve a desired bonding strength, in particular for bonding the topsheet through the one or more channels in the distribution layer to an underlying layer.

The absorbent articles may thus be packaged compressed at an In-Bag Compression Rate of at least 10%, in particular of from 10% to 50%, in particular of from 20% to 40%. The "In-Bag Compression Rate" as used herein is one minus the height of a stack of at least 10 folded articles measured while under compression within a bag ("In-Bag Stack Height") divided by the height of the stack of the same number of folded articles before compression, multiplied by 100; i.e. (1-In-Bag Stack Height/stack height before compression) *100, reported as a percentage. The articles before compression are sampled from the production line between the folding unit and the stack packing unit. The stack height before compression is measured by taking at least 10 articles before compression and packing, and measuring their stack height as indicated for the IBSH.

Relations Between the Layers and Components

Typically, adjacent layers will be joined together using conventional bonding method such as adhesive coating via slot coating or spraying on the whole or part of the surface of the layer, or thermo-bonding, or pressure bonding or combinations thereof. Most of the bonding between components is for clarity and readability not represented in the Figure, except in the cross-sectional views wherein some of the glue layers are indicated by dotted lines. Bonding between the layers of the article should be considered to be present unless specifically excluded. Adhesives may be typically used to improve the adhesion of the different layers, for example between the backsheet and the core wrap. The adhesives used may be any standard hotmelt glue as known in the art. The individual components may be converted into an absorbent article according to any of the processes known in the art.

The channels 86 in the distribution layer may also be used to bond an underlying with overlying layer. For example, as represented on FIG. 9, a topsheet layer 24 and/or an acquisition layer 52 can be attached directly or indirectly to an absorbent core 28 through the channels in the fibrous layer 54.

Misc

Unless indicated otherwise, the description and claims refer to the absorbent core and article before use (i.e. dry, and not loaded with a fluid) and conditioned at least 24 hours at 21° C.+/−2° C. and 50+/−5% Relative Humidity (RH).

As used herein, the terms "comprise(s)" and "comprising" are open-ended; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "preferably", "advantageously", "in particular", "optionally" and the likes also qualify features which are not intended to limit the scope of the claims unless specifically indicated to do so.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A process for making individual fibrous layers, the process comprising the steps of:
providing a first moving endless surface comprising a plurality of molds, wherein each mold comprises at least one raised element forming a rib-like element wherein neighboring molds are connected by a connecting section, wherein the connecting section comprises a width that is smaller than that of the molds it is connecting, wherein each connecting section is laterally delimited by two fingers pointing to each other, with the base of each finger having two rounded corners, wherein the radius of curvature of one of the rounded corners on each finger is larger than the radius curvature of the other corner on said finger;

continuously depositing fibrous material in the molds and the connecting sections to form a continuous fibrous layer, wherein the deposition of the fibers is hindered on the raised element;

transferring the continuous layer of the fibrous material from the first moving endless surface to a second moving endless surface; then cutting the continuous fibrous layer through the areas corresponding the connecting sections to form individual fibrous layers;

wherein the individual fibrous layers comprise at least one channel corresponding to the raised element in the mold and the channel is free of the fibrous material and extends through the whole thickness of the fibrous layer.

2. A process according to claim 1, wherein the first moving endless surface is a rotating deposition drum and the surface of the molds and of the connecting sections are linked to a negative pressure so that the fibers are drawn into the molds and the connecting sections during the deposition phase.

3. A process according to claim 2, wherein the surface of the raised elements are not linked to the negative pressure.

4. A process according to claim 1, wherein the continuous layer of fibrous material is placed and carried on a continuous support layer carried by the second endless moving surface, and wherein the continuous support layer is cut at the same time as the continuous fibrous layer to form individual laminates comprising an individual support layer supporting an individual fibrous layer.

5. A process according to claim 1, wherein the fibrous material comprises cellulose fibers.

6. A process according to claim 1, wherein each mold comprises at least one raised element which has the same shape and position in every mold.

7. A process according to claim 1, wherein the at least one raised element does not extend to any of the walls of the molds.

8. A process according to claim 1, wherein the at least one channel in the individual fibrous layers extends more longitudinally than transversally.

9. A process according to claim 1, wherein each individual fibrous layer comprises a pair of longitudinally-oriented channels.

10. A process according to claim 9, wherein the channels are discrete or are connected to each other.

11. A process according to claim 1, further comprising the step of attaching directly or indirectly the individual fibrous layer to an absorbent core.

12. A process according to claim 11, wherein the absorbent core comprises an absorbent layer comprised in a core wrap, and the absorbent material comprises superabsorbent particles.

13. A process according to claim 12, wherein the absorbent core comprises from 40% to 80% of superabsorbent polymers, by weight of the absorbent material, and cellulosic fibers.

14. A process according to claim 1, further comprising the step of attaching two layers through the channel.

15. A process according to claim 14, wherein a topsheet layer is attached directly or indirectly to an absorbent core through the channel in the fibrous layer.

16. A process according to claim 14, wherein an acquisition layer is attached directly or indirectly to an absorbent core through the channel in the fibrous layer.

* * * * *